(12) United States Patent
Prokash et al.

(10) Patent No.: US 7,922,983 B2
(45) Date of Patent: Apr. 12, 2011

(54) STERILIZATION WRAP WITH ADDITIONAL STRENGTH SHEET

(75) Inventors: Holly Prokash, Alpharetta, GA (US);
Maya Aroch, Malverne, NY (US);
Clarita Lewis, Dunwoody, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 971 days.

(21) Appl. No.: 11/192,442

(22) Filed: Jul. 28, 2005

(65) Prior Publication Data

US 2007/0026472 A1    Feb. 1, 2007

(51) Int. Cl.
*A61L 2/00*    (2006.01)
(52) U.S. Cl. ............ 422/294; 422/292; 422/26; 422/28
(58) Field of Classification Search ............... 422/28, 422/292, 294, 26
See application file for complete search history.

(56) References Cited

U.S. PATENT DOCUMENTS

| | | |
|---|---|---|
| 1,999,169 A | 4/1935 | Jackson |
| 2,627,341 A | 2/1953 | Morgan |
| 2,862,251 A | 12/1958 | Kalwaites |
| 2,917,878 A | 12/1959 | Carnarius et al. |
| 2,927,350 A | 3/1960 | Nelson |
| 3,137,387 A | 6/1964 | Overment |
| 3,183,557 A | 5/1965 | Hollowell |
| 3,338,992 A | 8/1967 | Kinney |
| 3,341,394 A | 9/1967 | Kinney |
| 3,403,776 A | 10/1968 | Denny |
| 3,484,330 A | 12/1969 | Sokolowski et al. |
| 3,485,706 A | 12/1969 | Evans |
| 3,502,763 A | 3/1970 | Hartmann |
| 3,542,615 A | 11/1970 | Dobo et al. |
| 3,595,465 A | 7/1971 | Vaillancourt |
| 3,604,616 A | 9/1971 | Greif |
| 3,628,743 A | 12/1971 | Lehyman et al. |
| 3,650,393 A | 3/1972 | Reiss et al. |
| 3,682,734 A | 8/1972 | Burger |
| 3,682,755 A | 8/1972 | Lee |
| 3,692,618 A | 9/1972 | Dorschner et al. |
| 3,716,961 A | 2/1973 | Cope et al. |
| 3,761,013 A | 9/1973 | Schuster |
| 3,768,725 A | 10/1973 | Pilaro |
| 3,780,857 A | 12/1973 | Rosano, Jr. et al. |
| 3,802,817 A | 4/1974 | Matsuki et al. |

(Continued)

FOREIGN PATENT DOCUMENTS

CA    724011 A    12/1965
(Continued)

OTHER PUBLICATIONS

Association for the Advancement of Medical Instrumentation dated 2005, pp. 55 & 56.

(Continued)

*Primary Examiner* — Sean E Conley
(74) *Attorney, Agent, or Firm* — Dority & Manning, P.A.

(57) ABSTRACT

A sterilization wrap is provided. The sterilization wrap includes a first sheet that is configured for providing a barrier to prevent at least some bacteria from passing therethrough while allowing sterilization gas to pass therethrough. A second sheet is attached to the first sheet. The second sheet is located on the first sheet so that a perimeter of the second sheet is contained entirely within a perimeter of the first sheet.

24 Claims, 4 Drawing Sheets

U.S. PATENT DOCUMENTS

| | | |
|---|---|---|
| 3,809,077 A | 5/1974 | Hansen |
| 3,849,241 A | 11/1974 | Butin et al. |
| 3,903,335 A | 9/1975 | Jones |
| 3,911,499 A | 10/1975 | Benevento et al. |
| 3,913,562 A | 10/1975 | Moore et al. |
| 3,926,309 A | 12/1975 | Center |
| 3,956,048 A | 5/1976 | Nordgren |
| 4,041,203 A | 8/1977 | Brock et al. |
| 4,042,655 A | 8/1977 | Platt et al. |
| 4,057,144 A | 11/1977 | Schuster |
| 4,057,203 A | 11/1977 | Newman et al. |
| 4,084,464 A | 4/1978 | Bowers |
| 4,091,921 A | 5/1978 | Lewis |
| 4,105,381 A | 8/1978 | Platt et al. |
| 4,116,338 A | 9/1978 | Weichselbaum |
| 4,146,133 A | 3/1979 | Bogorad et al. |
| 4,151,023 A | 4/1979 | Platt et al. |
| 4,154,889 A | 5/1979 | Platt |
| 4,169,123 A | 9/1979 | Moore et al. |
| 4,188,436 A | 2/1980 | Ellis et al. |
| 4,196,245 A | 4/1980 | Kitson et al. |
| 4,203,520 A | 5/1980 | Schuster |
| 4,206,844 A | 6/1980 | Thukamoto et al. |
| 4,213,812 A | 7/1980 | Boultinghouse |
| 4,270,658 A | 6/1981 | Schuster |
| 4,287,251 A | 9/1981 | King et al. |
| 4,337,223 A | 6/1982 | Kaye |
| 4,340,563 A | 7/1982 | Appel et al. |
| 4,342,390 A | 8/1982 | Mitchell et al. |
| 4,342,392 A | 8/1982 | Cox |
| 4,344,999 A | 8/1982 | Gohlke |
| 4,355,066 A | 10/1982 | Newman |
| 4,379,192 A | 4/1983 | Wahlquist |
| 4,380,485 A | 4/1983 | Schuster |
| 4,407,874 A | 10/1983 | Gehrke |
| 4,416,936 A | 11/1983 | Erickson et al. |
| 4,466,552 A | 8/1984 | Butterworth et al. |
| 4,470,153 A | 9/1984 | Kenan |
| 4,508,113 A | 4/1985 | Malaney |
| 4,511,035 A | 4/1985 | Alpern |
| 4,522,203 A | 6/1985 | Mays |
| 4,523,679 A | 6/1985 | Paikoff et al. |
| 4,535,481 A | 8/1985 | Ruth-Larson et al. |
| 4,550,546 A | 11/1985 | Raley et al. |
| 4,555,811 A | 12/1985 | Shimalla |
| 4,618,524 A | 10/1986 | Groitzsch et al. |
| 4,644,586 A | 2/1987 | Padgett |
| 4,652,763 A | 3/1987 | Nablo |
| 4,657,804 A | 4/1987 | Mays et al. |
| 4,660,721 A | 4/1987 | Mykleby |
| 4,705,171 A | 11/1987 | Eldridge |
| 4,714,595 A | 12/1987 | Anthony et al. |
| 4,773,532 A | 9/1988 | Stephenson |
| 4,793,483 A | 12/1988 | Holmes |
| 4,844,259 A | 7/1989 | Glowczewskie, Jr. et al. |
| 4,863,785 A | 9/1989 | Berman et al. |
| 4,874,090 A | 10/1989 | Dyke |
| 4,889,231 A | 12/1989 | Foote et al. |
| 4,904,520 A | 2/1990 | Dumas et al. |
| 5,028,468 A | 7/1991 | Taylor |
| 5,065,863 A | 11/1991 | Moyet-Ortiz |
| 5,072,832 A | 12/1991 | Valentine et al. |
| 5,137,600 A | 8/1992 | Barnes et al. |
| 5,156,743 A | 10/1992 | Muncrief |
| 5,165,539 A | 11/1992 | Weber et al. |
| 5,178,932 A | 1/1993 | Perkins et al. |
| 5,188,885 A | 2/1993 | Timmons et al. |
| 5,213,881 A | 5/1993 | Timmons et al. |
| 5,217,772 A | 6/1993 | Brown et al. |
| 5,222,507 A | 6/1993 | Taylor |
| 5,222,600 A | 6/1993 | Stoddard et al. |
| 5,229,191 A | 7/1993 | Austin |
| 5,244,718 A | 9/1993 | Taylor et al. |
| 5,271,883 A | 12/1993 | Timmons et al. |
| 5,283,106 A | 2/1994 | Sieler et al. |
| 5,294,482 A | 3/1994 | Gessner |
| 5,320,891 A | 6/1994 | Levy et al. |
| 5,415,925 A | 5/1995 | Austin et al. |
| 5,454,145 A | 10/1995 | Wattel et al. |
| 5,464,688 A | 11/1995 | Timmons et al. |
| 5,475,903 A | 12/1995 | Collins |
| 5,482,765 A | 1/1996 | Bradley et al. |
| 5,484,645 A | 1/1996 | Lickfield et al. |
| 5,503,907 A | 4/1996 | Gessner et al. |
| D369,907 S | 5/1996 | Sayovitz et al. |
| 5,547,746 A | 8/1996 | Burton, Sr. |
| 5,549,868 A | 8/1996 | Carlson, II |
| 5,554,435 A | 9/1996 | Gupta et al. |
| 5,593,768 A | 1/1997 | Gessner |
| 5,635,134 A | 6/1997 | Bourne et al. |
| 5,688,157 A | 11/1997 | Bradley et al. |
| 5,695,595 A | 12/1997 | Van Hout et al. |
| 5,698,294 A | 12/1997 | Van Hout et al. |
| 5,804,512 A | 9/1998 | Lickfield et al. |
| 5,857,467 A | 1/1999 | Faries, Jr. et al. |
| 5,879,620 A | 3/1999 | Cohen |
| 6,277,479 B1 | 8/2001 | Campbell et al. |
| 6,406,674 B1 | 6/2002 | Bourne et al. |
| 6,767,509 B1 | 7/2004 | Griesbach et al. |
| 2005/0079093 A1 | 4/2005 | Cannady et al. |
| 2005/0163654 A1 * | 7/2005 | Stecklein et al. ............ 422/28 |

FOREIGN PATENT DOCUMENTS

| | | |
|---|---|---|
| DE | 3835016 A1 | 4/1990 |
| EP | 0155149 A2 | 9/1985 |
| EP | 0155149 A3 | 9/1985 |
| EP | 0212540 A2 | 3/1987 |
| EP | 0212540 A3 | 3/1987 |
| EP | 0294178 A2 | 12/1988 |
| EP | 0294178 A3 | 12/1988 |
| EP | 0307173 A1 | 3/1989 |
| EP | 0398611 A1 | 11/1990 |
| EP | 0405793 A2 | 1/1991 |
| EP | 0405793 A3 | 1/1991 |
| EP | 0432586 A2 | 6/1991 |
| EP | 0432586 A3 | 6/1991 |
| EP | 0663967 B1 | 7/1995 |
| EP | 0754796 A1 | 7/1995 |
| FR | 2462351 | 2/1981 |
| GB | 671889 | 5/1952 |
| GB | 1017629 | 1/1966 |
| GB | 1053955 | 1/1967 |
| GB | 1241945 | 8/1971 |
| GB | 1488326 | 10/1977 |
| GB | 1519172 | 7/1978 |
| GB | 2029363 A | 3/1980 |
| GB | 1583760 | 2/1981 |
| GB | 2132939 A | 7/1984 |
| GB | 2229110 A | 9/1990 |
| JP | S6351721 | 4/1988 |
| JP | H1138733 | 9/1989 |
| JP | H285174 | 3/1990 |
| WO | WO 8911392 A1 | 11/1989 |
| WO | WO 9000643 A2 | 1/1990 |
| WO | WO 9000643 A3 | 1/1990 |
| WO | WO 9102643 A1 | 3/1991 |
| WO | WO 9205074 A1 | 4/1992 |
| WO | WO 9310300 A1 | 5/1993 |
| WO | PCT 2005 037333 A1 | 4/2005 |

OTHER PUBLICATIONS

EPO Search Report, Sep. 5, 2006.
Japanese Abstract for JP3294559, Dec. 25, 1991.

* cited by examiner

STERILIZATION WRAP WITH ADDITIONAL STRENGTH SHEET

BACKGROUND

Personnel in the Central Service Room (CSR) or the Sterile Processing Department (SPD) of hospitals are charged with the responsibility of packaging surgical supplies to ensure the sterility of the packaged contents from the point of sterilization to the point of reuse. Surgical supplies that are candidates for being reused include clamps, scalpel blade handles, retractors, forceps and scissors. These supplies can be placed in stainless steel instrument trays while softer goods such as surgeon towels, drapes and gowns are packaged. The instrument tray and package are generally wrapped with two sheets of material commonly known as sterilization wrap.

The sterilization wrap is usually a woven or a nonwoven material that is wrapped around the tray or package in a certain prescribed manner to permit entry of sterilizing vapor/gas for sterilization purposes while denying ingress of contaminants such as bacteria and other infectious causing material. Current sterilization procedures often call for double wrapping in that the contents are wrapped into two sterilization sheets either sequentially or simultaneously. The sterilization-wrapped package is placed into an autoclave that sterilizes the contents by heat and steam. Alternatively, ethylene oxide sterilization or hydrogen peroxide gas plasma sterilization may be employed.

After sterilization, the sterilization wrap and associated contents are typically taken to a prescribed area for storage. Subsequently, the wrapped package may be taken to the point of use and the wrap removed. Tears or holes in the sterilization wrap that may occur at various points from sterilization to use may compromise the contents. For example, if a large number of instruments are placed into the instrument tray for sterilization the resulting weight on the sterilization wrap could be from 25 to 30 pounds (11.34 kg to 13.61 kg) or more. Sterilization wraps with sterilized contents are sometimes placed onto wire shelves for storage. Sliding of the sterilization wrap with the sterilized contents may cause tearing of the sterilization wrap and necessitate a repeat of the sterilization procedure with a new sterilization wrap.

SUMMARY

Various features and advantages of the invention will be set forth in part in the following description, or may be obvious from the description, or may be learned from practice of the invention.

The present invention provides for a sterilization wrap that may be used in a sterilization procedure for sterilizing instrument trays, instruments, and other items. The sterilization wrap includes a first sheet that allows sterilization gas but prevents bacteria from passing therethrough. A second sheet is attached to the first sheet and is located on the first sheet so that the perimeter of the second sheet is contained entirely within the perimeter of the first sheet. The second sheet provides added strength to the sterilization wrap to prevent the instrument tray, instruments or other items wrapped and stored by the sterilization wrap from tearing or ripping therethrough during use and/or storage.

The second sheet may be configured in other exemplary embodiments for providing a barrier to prevent bacteria from passing therethrough. The second sheet may have a higher basis weight than the first sheet in accordance with certain exemplary embodiments so as to provide additional strength to the sterilization wrap.

The first sheet may be a laminate formed from a meltblown layer positioned between a pair of spunbonded layers. Additionally, the first sheet may include a pair of the aforementioned laminates that are joined to one another by a plurality of spaced apart and separate bond points. Each of the laminates has a basis weight of from about 0.5 to about 3.5 ounces per square yard (16.96 gsm to 118.69 gsm). Such a configuration of the sterilization wrap is commonly known as a "one step" wrap in that a double wrapping is effected through a single wrapping procedure since a pair of laminates in the first sheet are present. Alternatively, the first sheet may be a single laminate as previously stated. Here, double wrapping may be effected through either a sequential or simultaneous process.

The first and second sheets may be variously sized and oriented with respect to one another in accordance with different exemplary embodiments. For example, both the first and second sheets may have a rectangular shaped upper surface. The second sheet may be oriented on the first sheet so that the sides of the second sheet are oriented generally at 45° angles to the sides of the first sheet. The relative size of the area of the upper surfaces of the first and second sheets may be varied. For example, the surface area of the second sheet may be from 27% to 54% of the surface area of the first sheet in accordance with one exemplary embodiment.

The first and second sheets may be attached to one another so that the second sheet does not move with respect to the first sheet during placement, wrapping, storage and transportation of the instrument trays, instruments or items desired for sterilization. Attachment between the first and second sheets may be effected through a variety of mechanisms such as adhesives, hook and loop type fasteners, tape, and bonding.

These and other features, aspects and advantages of the present invention will become better understood with reference to the following description and appended claims. The accompanying drawings, which are incorporated in and constitute part of this specification, illustrate embodiments of the invention, and together with the description serve to explain the principles of the invention.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
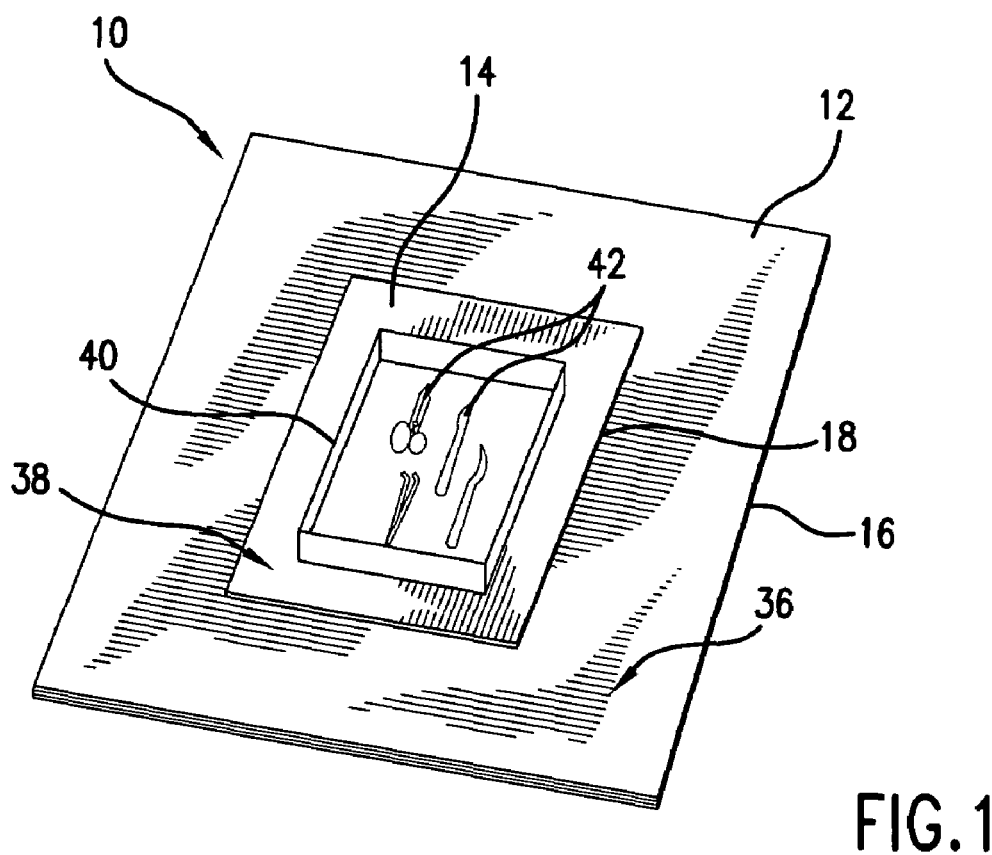
FIG. 1 is a perspective view of a sterilization wrap in accordance with one exemplary embodiment.

Repeat use of reference characters in the present specification and drawings is intended to represent the same or analogous features or elements of the invention.

DEFINITIONS

As used herein, the term "nonwoven" means a web having a structure of individual fibers or threads which are interlaid, but not in an identifiable manner as in a knitted fabric. Nonwoven fabrics or webs have been formed from various processes such as, for example, meltblowing processes, spunbonding processes, and bonded carded web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91).

As used herein, the term "spunbonded or spunbond" refers to small diameter fibers which are formed by extruding molten thermoplastic material as filaments from a plurality of fine, usually circular capillaries of a spinneret with the diameter of the extruded filaments then being rapidly reduced to fibers as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al., the contents of which are incorporated herein by reference in their entirety. Spunbond fibers are generally continuous and have diameters generally greater than about 7 microns, more particularly, between about 10 and about 20 microns. As used herein, the term "meltblown" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Butin et al., the content of which is incorporated herein by reference in its entirety. Meltblown fibers are microfibers which may be continuous or discontinuous with diameters generally less than 10 microns.

As used herein, the term "bicomponent" refers to fibers that can be made from a method of extruding two polymers from the same spinneret with both polymers contained within the same filament.

DETAILED DESCRIPTION OF REPRESENTATIVE EMBODIMENTS

Reference will now be made in detail to embodiments of the invention, one or more examples of which are illustrated in the drawings. Each example is provided by way of explanation of the invention, and not meant as a limitation of the invention. For example, features illustrated or described as part of one embodiment can be used with another embodiment to yield still a third embodiment. It is intended that the present invention include these and other modifications and variations.

It is to be understood that the ranges mentioned herein include all ranges located within the prescribed range. As such, all ranges mentioned herein include all sub-ranges included in the mentioned ranges. For instance, a range from 100-200 also includes ranges from 110-150, 170-190, and 153-162. Further, all limits mentioned herein include all other limits included in the mentioned limits. For instance, a limit of up to 7 also includes a limit of up to 5, up to 3, and up to 4.5.

A sterilization wrap 10 is provided that is used in a sterilization procedure for sterilizing surgical instruments and supplies. Sterilization wrap 10 is made of a first sheet 12 that can be either a single layer or laminate or may be a double layer or laminate. A second sheet 14 is attached to the first sheet 12 such that instrument trays 40, instruments 42, and other items desired for sterilization may be placed thereon. The second sheet 14 provides strength to the sterilization wrap 10 so as to resist tearing or strike through of the sterilization wrap 10 by the items placed onto the sterilization wrap 10 during transport or storage.

An exemplary embodiment of the sterilization wrap 10 is shown in FIG. 1. As shown, an instrument tray 40 having instruments 42 therein is placed onto the sterilization wrap 10 that is made of the first and second sheets 12 and 14. The second sheet 14 provides an additional layer of strength and durability to the sterilization wrap 10 during initial wrapping, sterilization, transportation, and storage of the sterilization wrap 10. The second sheet 14 can be variously shaped and sized in order to accommodate variously sized items to be sterilized.

The first sheet 12 may be any type of material used in sterilization wraps 10. For example, the first sheet 12 may be a woven material such as cloth made from cotton and/or polyester. The first sheet 12 may also be made of non-woven materials such as KIMGUARD® Sterilization Wrap available from Kimberly-Clark Corporation of Neenah, Wis. The first sheet 12 may be a single layer of material or may be a laminate such as a spunbonded/meltblown laminate or a spunbonded/meltblown/spunbonded laminate. Various types of material that can be used in construction of the first sheet 12 and associated methods of manufacture may be found in U.S. Pat. Nos. 5,879,620; 6,406,674; and 6,767,509; the entire contents of which are incorporated by reference herein in their entirety for all purposes.

The second sheet 14 is an additional layer or laminate that is applied to the first sheet 12 in order to impart improved strength characteristics. The second sheet 14 may be made of the same material as the first sheet 12 or may be constructed of a different material. For example, the second sheet 14 may be made from a foam, a woven-web, a high loft material, and/or a bicomponent spunbond material in accordance with various exemplary embodiments. The second sheet 14 may be bicomponent spunbond material made of varying polymers such as nylon, PET, etc. The material selected for the second sheet 14 may be selected so as to withstand the temperature imparted thereon during sterilization.

The second sheet 14 is arranged on the first sheet 12 so that the perimeter 18 of the second sheet 14 is contained entirely within the perimeter 16 of the first sheet 12. As such, the area of the upper surface 38 is less than the area of the upper surface 36. The size of the second sheet 14 is smaller than the first sheet 12 such that excess material is not needed in order to avoid associated costs while at the same time providing sufficient strengthening of the sterilization wrap 10.

Figure 2:
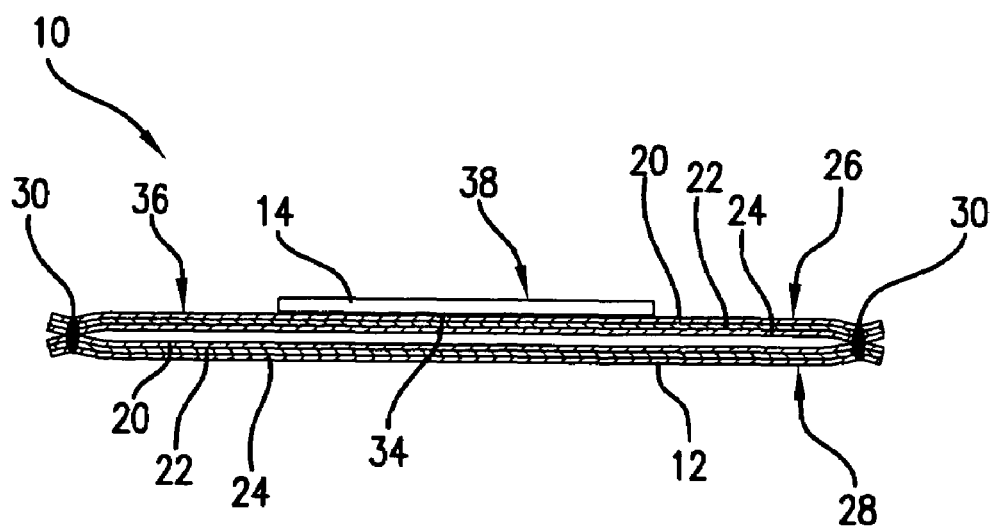
FIG. 2 is a side view of a sterilization wrap that has a first sheet with a pair of laminates in accordance with one exemplary embodiment.

FIG. 2 is a side view of the sterilization wrap 10 in which the first sheet 12 is made from a pair of laminates 26 and 28. This type of sterilization wrap 10 is disclosed in U.S. Pat. No. 6,406,674. As shown, the first sheet 12 is "double layer" in which the laminates 26 and 28 are attached to one another through a plurality of spaced apart and separate bond points 30 so that the user is aware of the fact that a pair of laminates 26 and 28 make up the first sheet 12. In this regard, the user may sterilize items in a single step as the first sheet 12 provides a "double layer" of protection. In alternative wrapping methods, the first sheet 12 is a single layer thus requiring the medical technician to either place two sterilization wraps 10 on top of one another and then wrap the item for sterilization, or to sequentially wrap a first sterilization wrap 10 and then a second sterilization wrap 10 in order to accomplish "double wrapping" as sometimes required by hospital procedure.

The laminates 26 and 28 may be each made of a meltblown layer 22 positioned between a pair of spunbonded layers 20 and 24. Each of the laminates 26 and 28 may have a basis weight of from about 0.5 to about 3.5 ounces per square yard (16.96 gsm to 118.69 gsm). The first sheet 12 may be connected to the second sheet 14 through an attachment 34. The attachment 34 may be, for example, adhesive, hook and loop type fasteners, tape, and/or bonding in accordance with various exemplary embodiments. The attachment 34 may be capable of holding the position of the second sheet 14 stationary with respect to the first sheet 12 so that a known location for positioning the items to be sterilized is provided. The attachment 34 may be used in order to securely locate the position of the second sheet 14 onto the upper surface 36 of the first sheet 12. This feature may ensure cushioning of the instrument tray 40, instruments 42 and other items as the second sheet 14 will not slide around or fold down thus leaving one or more upper corners or edges of the instrument tray 40, instruments 42, or other items without cushioning.

The attachment between the first and second sheets 12 and 14 may be over the entire area of the second sheet 14 or may be over less than the entire area of the second sheet 14. The attachment between the first and second sheets 12 and 14 may be at the perimeter 18 of the second sheet 14. The attachment at the perimeter 18 may be continuous or intermittent.

The second sheet 14 may have a porosity that is the same as or greater than that of the first sheet 12. The porosity of the second sheet 14 may be selected to allow for sterilization gas, but not bacteria, to pass therethrough. Alternatively, the second sheet 14 may be selected so as to have a porosity that allows for both sterilization gas and bacteria to pass therethrough. In this instance, the first sheet 12 will protect the items from contamination as the first sheet 12 prevents bacteria from passing therethrough.

Figure 3:
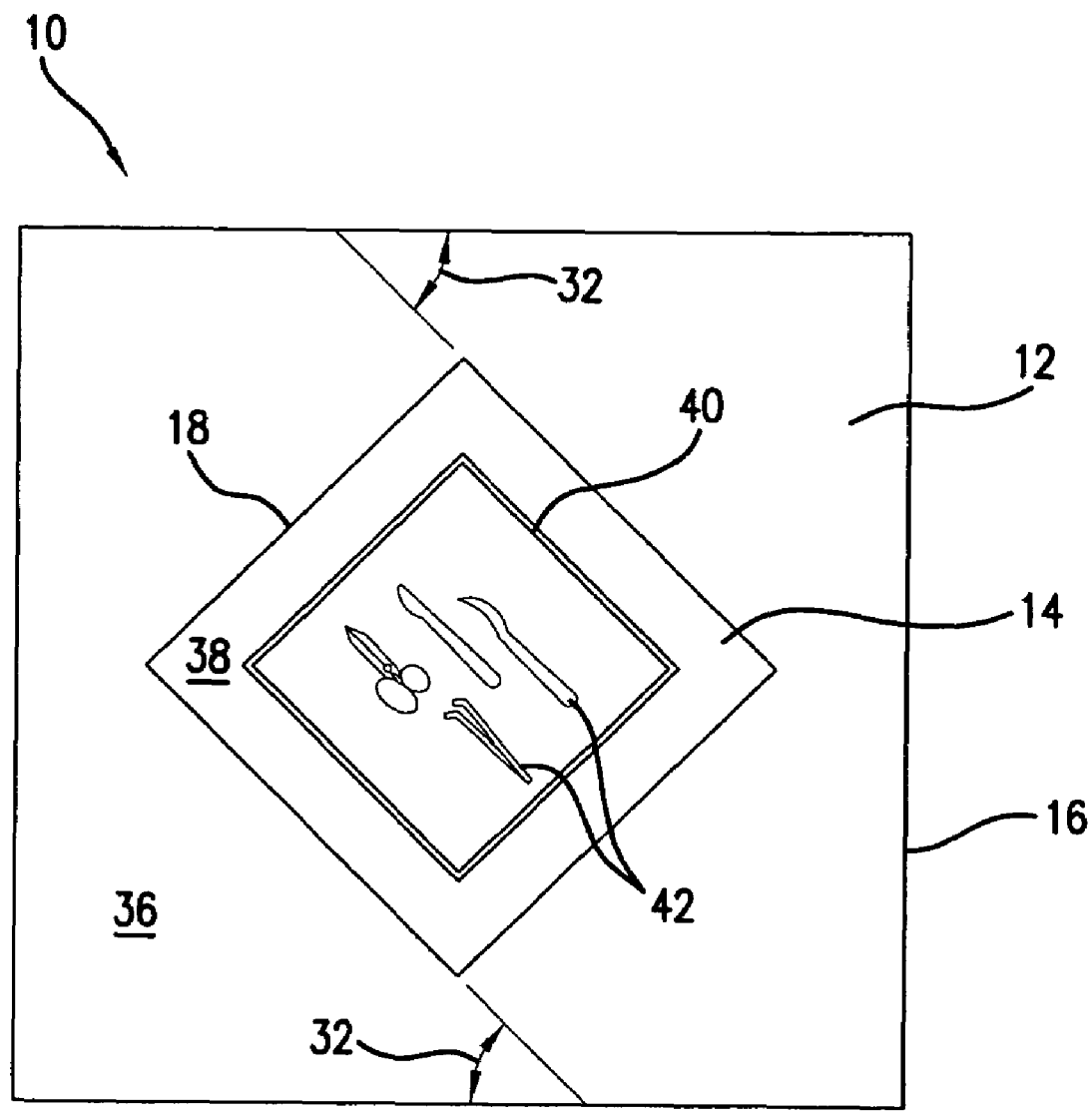
FIG. 3 is a top view of a sterilization wrap in which the second sheet is oriented at an angle to the first sheet in accordance with one exemplary embodiment.
Figure 4A:
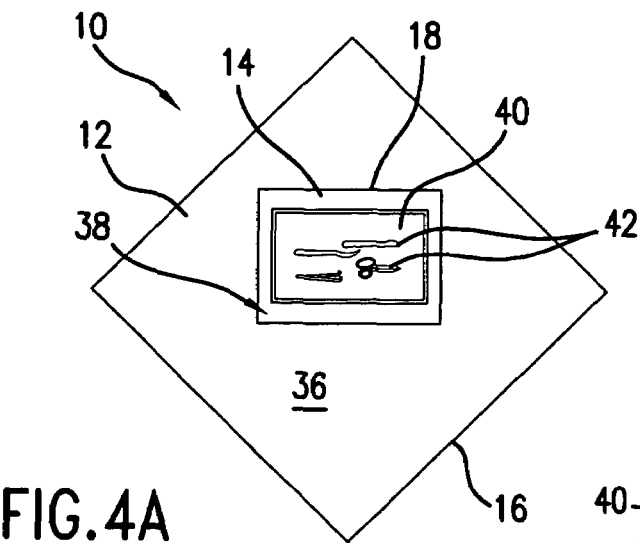
FIGS. 4A-4E show a method of folding an exemplary embodiment of the sterilization wrap into an envelope fold.
Figure 4B:
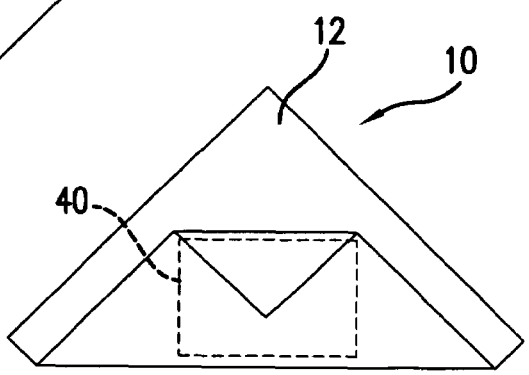
Figure 4C:
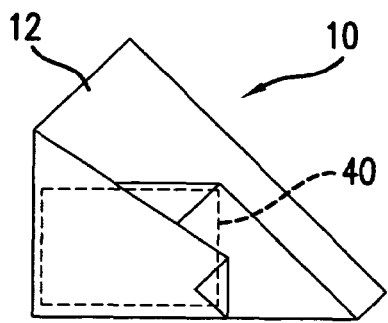
Figure 4D:
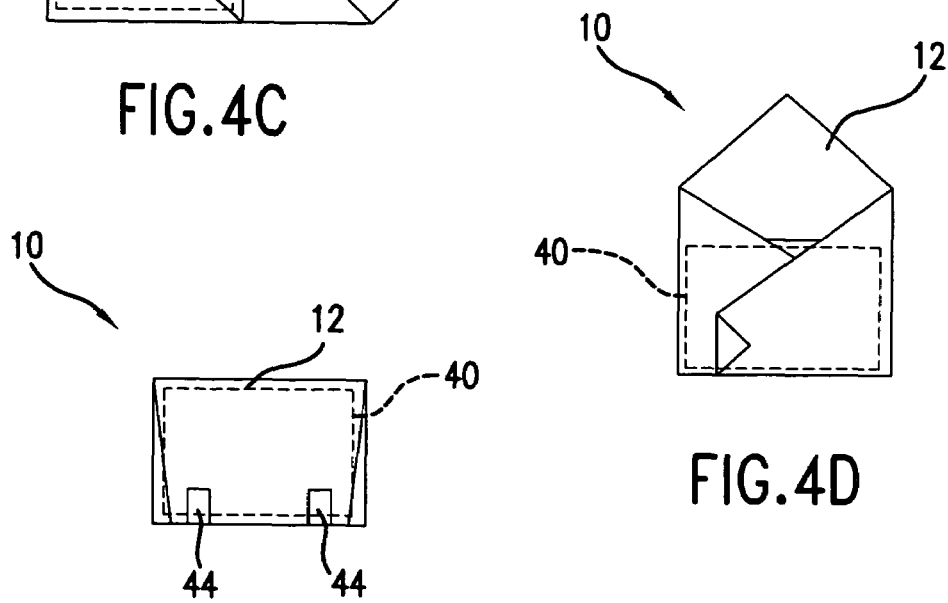
Figure 4E:
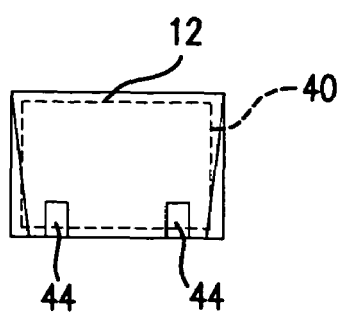

FIG. 3 shows one exemplary embodiment of the sterilization wrap 10 in which the second sheet 14 is attached to the upper surface 36 of the first sheet 12. An instrument tray 40 along with various instruments 42 are placed onto the upper surface 38 of the second sheet 14. The upper surface 36 of the first sheet 12 is defined by a perimeter 16. The area of the upper surface 36 is obtained upon multiplying the length and height of the sides of the first sheet 12. The second sheet 14 also has a perimeter 18 that defines the upper surface 38 of the second sheet 14. The area of the upper surface 38 is obtained upon multiplying the length and height of the sides of the second sheet 14. It is to be understood, however, that if the first and second sheets 12 and 14 are not configured as rectangles, in accordance with other exemplary embodiments, that the areas of the upper surfaces 36 and 38 will be calculated in a different manner.

The second sheet 14 is shown attached to approximately the center of the upper surface 36 and is oriented with respect to the first sheet 12 so as to have sides that are at an angle 32 to the sides of the first sheet 12. In the exemplary embodiments shown in FIG. 3, the angle 32 is 45°. In accordance with other exemplary embodiments, however, the angle 32 may be from 20° to 70°.

The second sheet 14 may be attached to the first sheet 12 during the manufacturing process so that the end user will not need to attach the first and second sheets 12 and 14 to one another upon using the sterilization wrap 10. Alternatively, the second sheet 14 may be sold as a separate element that can be separately attached to the first sheet 12 of a sterilization wrap 10 as desired on an as-needed basis. The user may attach the second sheet 14 to the first sheet 12 to provide for a stronger sterilization wrap 10 if, for instance, the sterilization of heavier instrument trays 40 and/or instruments 42 is needed. If attached during the manufacturing process, the attachment 34 may be made, for example, by adhesives or hook and loop type fasteners. If the second sheet 14 is provided separately, the attachment 34 may be effected through hook and loop type fasteners and/or tape.

Table 1 shows various dimensions of the first sheet 12 and the second sheet 14 that are capable of covering and cushioning variously sized and shaped instrument trays 40, instruments 42, and other items.

TABLE 1

| 1<br>First Sheet 12 Size | 2<br>Size of Item Being Wrapped | 3<br>Necessary Dimensions for Cushioning | 4<br>Total Area of First Sheet 12 | 5<br>Total Area of Cushioning/Second Sheet 14 (using maximum dimension) | 6<br>% of Wrap Area Needed for Cushioning |
|---|---|---|---|---|---|
| 20" × 20"<br>(50.80 cm × 50.8 cm) | 6" diameter × 3"<br>(15.24 cm × 7.62 cm)<br>deep Round Basin | 8.5" × 8.5" (21.59 cm × 21.59 cm) | 400 sq. in.<br>(2580 sq. cm.) | 72.25 sq. in.<br>(466 sq. cm) | 18% |
| 24" × 24"<br>(60.69 cm × 60.69 cm) | 7.25" × 2.5" × 0.25" (18.41 cm × 6.35 cm × 0.64 cm) Individual Instrument 42 | 15" × 7"<br>(38.1 cm × 17.78 cm) (to cushion edges only) | 576 sq. in.<br>(3715.2 sq. cm.) | 225 sq. in.<br>(1451.25 cm) | 39% |
| 24" × 24"<br>(60.69 cm × 60.69 cm) | 7.25" × 2.5" × 0.25" (18.41 cm × 6.35 cm × 0.64 cm) Individual Instrument 42 | 22" × 10"<br>(55.88 cm × 25.4 cm) (to cushion entire instrument) | 576 sq. in.<br>(3715.2 sq. cm.) | 484 sq. in.<br>(3121.8 sq. cm) | 84% |
| 30" × 30"<br>76.2 cm × 76.2 cm) | 9" × 8.5" × 2.25" (22.86 cm × 21.59 cm × 5.72 cm) Tray 40 | 15" × 15.5"<br>(38.1 cm × 39.37 cm) | 900 sq. in.<br>(5805 sq. cm) | 240.25 sq. in.<br>(1549.6 sq. cm) | 27% |
| 30" × 30"<br>76.2 cm × 76.2 cm) | 15" × 6" × 2" tray (38.1 cm × 15.24 cm × 5.08 cm) 40 | 22" × 13"<br>(55.88 cm × 33.02 cm) | 900 sq. in.<br>(5805 sq. cm) | 484 sq. in.<br>(3121.8 sq. cm) | 54% |
| 36" × 36"<br>(9144 cm × 91.44 cm) | 10" × 10.5" × 3.5" (25.4 cm × 26.67 cm × 8.89 cm) Tray 40 | 19.5" × 19.5"<br>(49.53 cm × 49.53 cm) | 1296 sq. in.<br>(8359.2 sq. cm) | 380.25 sq. in.<br>(2452.6 sq. cm) | 29% |
| 45" × 45" | 20.5" × 11" × | 27.5" × 18.25" | 2025 sq. in. | 756.25 sq. in. | 37% |

TABLE 1-continued

| 1<br>First Sheet 12 Size | 2<br>Size of Item Being Wrapped | 3<br>Necessary Dimensions for Cushioning | 4<br>Total Area of First Sheet 12 | 5<br>Total Area of Cushioning/Second Sheet 14 (using maximum dimension) | 6<br>% of Wrap Area Needed for Cushioning |
|---|---|---|---|---|---|
| (114.3 cm × 114.3 cm) | 3" (52.07 cm × 27.94 cm × 7.62 cm) Tray 40 | (69.85 cm × 46.36 cm) | (13,061.2 sq. cm) | (4877.8 sq. cm) | |
| 45" × 45" (114.3 cm × 114.3 cm) | 20" × 10.5" × 3.5" (50.8 cm × 26.67 cm × 8.89 cm) Tray 40 | 28.75" × 19.25" (73.03 cm × 48.90 cm) | 2025 sq. in. (13,061.2 sq. cm) | 826.5625 sq. in. (5331.35 sq. cm) | 41% |
| 45" × 45" (114.3 cm × 114.3 cm) | 21" × 10" × 3.5" (53.34 cm × 25.4 cm × 8.89 cm) Sterrad Tray 40 | 29.75" × 18.75" (75.57 cm × 47.63 cm) | 2025 sq. in. (13,061.2 sq. cm) | 885.0625 sq. in. (5708.65 sq. cm) | 44% |
| 45" × 45" (114.3 cm × 114.3 cm) | 14" diameter × 5" (35.56 cm × 12.7 cm) deep Round Basin | 20" × 20" (50.8 cm × 50.8 cm) | 2025 sq. in. (13,061.2 sq. cm) | 400 sq. in. (2580 sq. cm) | 20% |
| 48" × 48" (121.92 cm × 121.92 cm) | 20.5" × 10.5" × 4.5" (52.07 cm × 26.67 cm × 11.43 cm) Tray 40 | 30.5" × 21" (77.47 cm × 53.34 cm) | 2304 sq. in. (14,860.8 sq. cm) | 930.25 sq. in. (6000.1 sq cm) | 40% |

Column 1 shows the size of the first sheet 12. Here, the first sheet 12 is rectangular in all instances. Column 2 shows the size of the item, instrument tray 40, or instrument 42 that is to be wrapped by the sterilization wrap 10.

During a typical wrapping procedure, the instrument tray 40, instrument 42, or other item to be wrapped is typically placed at an angular orientation as shown for instance in FIG. 3. Column 3 in Table 1 shows the various dimensions that are needed for cushioning various instrument trays 40, instruments 42 and other items. This minimum area is calculated to provide cushioning on the bottom of the instrument tray 40, instrument 42, or other item and for potential problem areas such as top edges and corners on instrument trays 40 and the rims of basins. Although described as being oriented so as to have an angle 32, it is to be understood that the second sheet 14 may have sides that are aligned with the first sheet 12 in accordance with other exemplary embodiments. The second sheet 14 simply provides for cushioning and adequate coverage of the instrument tray 40, instrument 42, and other items to prevent tearing or other strike through of the sterilization wrap 10.

Column 4 in Table 1 is the area of the upper surface 36. This area is obtained upon multiplying the two dimensions shown in column 1. Column 5 shows the total area of cushioning and thus the area of the upper surface 38 of the second sheet 14. The area calculated in column 5 is obtained upon using the longest dimension in column 3. For example, if the dimensions of the cushioning area in column 3 is 15" by 15.5" (38.1 cm×39.37 cm) the longest dimension is 15.5" (39.37 cm) and thus the area calculated in column 5 is 15.5"×15.5" (39.37 cm×39.37 cm)=240.25 square inches (1550 sq cm).

Column 6 is the percentage of the area of the upper surface 36 of the first sheet 12 that must be covered by the area of the upper surface 38 of the second sheet 14 to provide for a desired cushioning. The percentage in column 6 are obtained upon dividing the area in column 5 by the area in column 4. For example, the first row in Table 1 shows the percentage of wrap area needed for cushioning to be 72.25 square inches (466 sq cm) divided by 400 square inches (2580 sq cm)=18%. Table 1 thus shows the percentage of area of the upper surface 36 of the first sheet 12 that must be covered by the second sheet 14 so as to provide for a desired cushioning of the more standard instrument trays 40, instruments 42, and other items that are typically sterilized with a sterilization wrap 10. As shown, the area of the upper surface 38 of the second sheet 14 may be from between 18% to 84% of the area of the upper surface 36 of the first sheet 12. However, a majority of the instrument trays 40, instruments 42, and items to be wrapped may only need an upper surface 38 that is from 27% to 54% of the upper surface 36 to provide for additional cushioning of the sterilization wrap 10.

Although described as being provided to cushion the top side edges and corners of the instrument tray 40, instruments 42, and other items wrapped in addition to the bottom edges and corners, the second sheet 14 may be sized to provided cushioning to less than the aforementioned portions of the instrument trays 40, instruments 42, and other items. Generally, the area of the upper surface 38 may be at least 30% of the area of the upper surface 36 in order to cushion substantially all standard instrument trays 40, instruments 42, and other items.

The second sheet 14 may be selected to be preferably low or non-linting as the second sheet 14 will be in close proximity to or in contact with the instrument tray 40, instruments 42, or other items. This property may help to prevent extraneous matter from residing in or on the instrument tray 40, instruments 42, or other items and may prevent lint from contaminating the operating room and/or surgical site. The second sheet 14 may be made from a relatively inexpensive material so as to be disposable along with the first sheet 12.

The second sheet 14 may have an absorbent property thereto in order to minimize pooling of excess moisture and to promote more efficient drying during certain sterilization processes. It is sometimes the case that moisture remains within the wrapped sterilization wrap 10 after sterilization. Moisture may promote the growth of microorganisms and hence necessitate a repeat of the sterilization procedure.

The folding methods shown in FIGS. 4A-4E and FIGS. 5A-5E are folding processes for sterilization wraps that have been set forth by the Association for the Advancement of Medical Instrumentation. FIGS. 4A-4E show a sterilization wrap 10 that is folded into an "envelope fold" for sterilization. Here, the second sheet 14, instrument tray 40, and instruments 42 are positioned off center of the upper surface 36 of the first sheet 12. The first sheet 12 may be made of a pair of laminates 26 and 28 as previously discussed so that the instrument tray 40 and instruments 42 are folded into the sterilization wrap 10 in a "single step process." Alternatively, a pair of first sheets 12 may be placed one on top of another and folded in the manner shown in FIGS. 4A-4E. The second sheet 14, in this instance, may be attached to only one of the first sheets 12 and not the other. Upon completion of the "envelope fold" shown in FIGS. 4A-4E, tape 44 may be used in order to close the sterilization wrap 10 for subsequent sterilization.

Figure 5A:
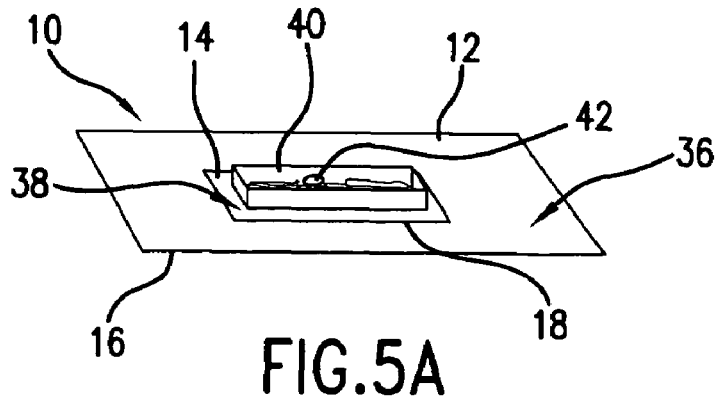
FIGS. 5A-5E show a method of folding an exemplary embodiment of the sterilization wrap into a square fold.
Figure 5B:
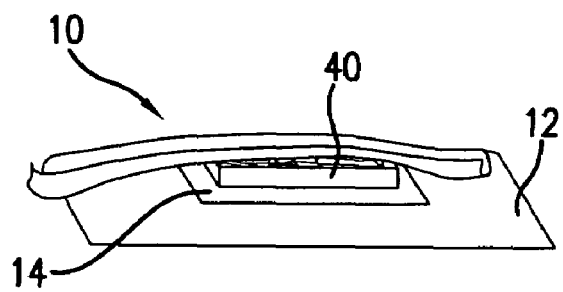
Figure 5C:
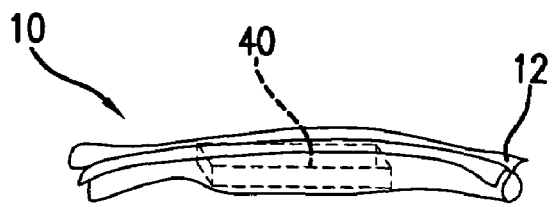
Figure 5D:
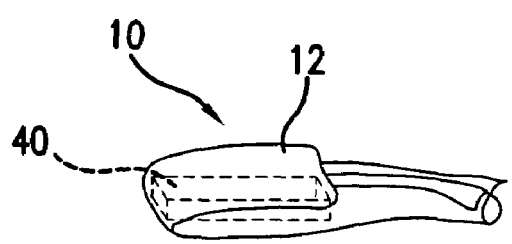
Figure 5E:
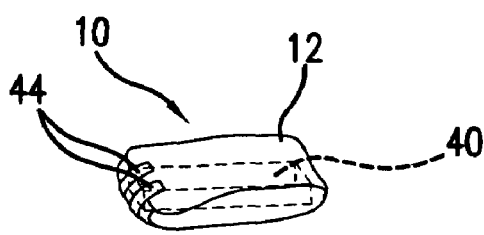

FIGS. 5A-5E demonstrate a folding process known as a "square fold." The first sheet 12 may again be made of pair of laminates 26 and 28 as previously discussed or may be made from a single layer or laminate in which case two of the first sheets 12 must be provided in order to achieve double wrapping of the sterilization wrap 10. If a pair of first sheets are provided, the second sheet 14 may be attached to only one of the first sheets 12. Upon folding of the instrument tray 40 and instruments 42, tape 44 is used to close the folded sterilization wrap 10 as shown in FIG. 5E.

The method of folding used and the orientation of the second sheet 14 on the first sheet 12 may dictate the size of the second sheet 14 needed for effecting the desired cushioning of the instrument tray 40, instruments 42, or other items. With respect to one orientation, both the first and second sheets 12 and 14 may be rectangular in shape and the sides of both the first and second sheets 12 and 14 may be parallel to one another. With respect to a second orientation, the second sheet 14 may be arranged as shown in FIG. 3 so that the corners of the second sheet 14 are centered along the edges of the first sheet 12 and so that an angle 32 of 45° is present. With respect to square or rectangular instruments trays 40, the coverage area of the second sheet 14 that is needed may be made smaller depending upon the particular orientation of the second sheet 14 and the wrapping method used. For example, if the envelope fold shown in FIGS. 4A-4E is used for wrapping the instrument tray 40, and if the second sheet 14 is oriented so as to have an angle 32 of 45°, the resulting area of the second sheet 14 needed to cushion the corners and upper edges of the instrument tray 40 is smaller than if the second sheet 14 had sides parallel to the sides of the first sheet 12. Conversely, if the square fold technique shown in FIGS. 5A-5E is employed, and if the second sheet 14 is oriented with sides parallel to the first sheet 12, the aforementioned cushioning may be accomplished with a lower area of the upper surface 38 of the second sheet 14 with respect to square or rectangular instrument trays 40 than if an angle 32 of 45° was present.

Sterilization may be accomplished through use of an autoclave that sterilizes through heat and steam. Additionally or alternatively, the instrument tray 40, instrument 42 or other items may be sterilized through the use of ethylene oxide and/or through the use of hydrogen peroxide gas plasma both of which are typically conducted with lower temperatures than if an autoclave were employed.

While the present invention has been described in connection with certain preferred embodiments, it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A sterilization wrap, comprising:
   a first sheet configured for providing a barrier so as to prevent at least some bacteria from passing therethrough, said first sheet configured to allow sterilization gas to pass therethrough, said first sheet having a perimeter, said first sheet comprising two laminates joined together, each laminate comprising a spunbonded layer, a meltblown layer, and a spunbonded layer; and
   a second sheet attached to said first sheet, said second sheet being oriented from 20° to 70° in relation to the sides of said first sheet, said second sheet having a perimeter and said second sheet located on said first sheet so that said perimeter of said second sheet is contained entirely within said perimeter of said first sheet, such that the surface area of said second sheet is less than 50% of the surface area of said first sheet.

2. The sterilization wrap as set forth in claim 1, wherein said second sheet is configured for providing a barrier so as to prevent at least some bacteria from passing therethrough.

3. The sterilization wrap as set forth in claim 1, wherein said second sheet has a higher porosity than said first sheet.

4. The sterilization wrap as set forth in claim 1, wherein said second sheet has a higher basis weight than said first sheet.

5. The sterilization wrap as set forth in claim 1, wherein the pair of laminates are joined by a plurality of spaced apart and separate bond points, and wherein each of the pair of laminates has a basis weight of from about 16.96 gsm to about 118.69 gsm.

6. The sterilization wrap as set forth in claim 1, wherein both said first and second sheets have a rectangular shaped upper surface, and wherein said second sheet is oriented on said upper surface of said first sheet such that the sides of said second sheet are oriented at 45° angles to the sides of said first sheet.

7. The sterilization wrap as set forth in claim 1, wherein the surface area of said second sheet is from 18% to 44% of the surface area of said first sheet.

8. The sterilization wrap as set forth in claim 1, wherein said second sheet is attached over the entire area of the bottom surface of said second sheet to said first sheet.

9. The sterilization wrap as set forth in claim 1, wherein said second sheet is attached over less than the entire area of the bottom surface of said second sheet to said first sheet.

10. The sterilization wrap as set forth in claim 1, wherein the perimeter of said second sheet is attached to said first sheet.

11. The sterilization wrap as set forth in claim 10, wherein the perimeter of said second sheet is attached intermediately to said first sheet.

12. A sterilization wrap, comprising:
   a first sheet adapted for use in a sterilization environment, said first sheet providing bacterial filtration to prevent at least some bacteria from passing therethrough, said first sheet configured to allow sterilization gas to pass therethrough for sterilizing objects, said first sheet having a perimeter and having an upper surface with a surface area, said first sheet includes a laminate that has a spunbonded layer, a meltblown layer, and a spunbonded layer; and
   a second sheet attached to said upper surface of said first sheet to provide strength so as to resist tearing therethrough, said second sheet being oriented from 20° to 70° in relation to the sides of said first sheet, said second sheet having a perimeter and said second sheet located on said first sheet so that said perimeter of said second sheet is contained entirely within said perimeter of said first sheet, said second sheet having an upper surface with a surface area, said surface area of said second sheet being less than 50% of the surface area of said first sheet said second sheet configured to allow sterilization gas to pass therethrough.

13. The sterilization wrap as set forth in claim 12, wherein said second sheet has a higher porosity than said first sheet.

14. The sterilization wrap as set forth in claim 12, wherein said second sheet has a higher basis weight than said first sheet.

15. The sterilization wrap as set forth in claim 14, wherein said second sheet has a basis weight greater than 118.69 gsm.

16. The sterilization wrap as set forth in claim 12, wherein said first sheet includes an additional laminate that has a spunbonded layer, a meltblown layer, and a spunbonded layer, and wherein said pair of laminates are joined by a plurality of spaced apart and separate bond points, and wherein each of the pair of laminates has a basis weight of from about 16.96 gsm to about 118.69 gsm.

17. The sterilization wrap as set forth in claim 12, wherein said first and second sheets are made from the same material.

18. The sterilization wrap as set forth in claim 12, wherein said second sheet is made from a material selected from the group consisting of a foam, a woven web, a high loft material, and a bicomponent spunbond.

19. The sterilization wrap as sot forth in claim 12, wherein said second sheet is attached over the entire area of the bottom surface of said second sheet to said first sheet.

20. The sterilization wrap as set forth in claim 12, wherein the perimeter of said second sheet is attached to said first sheet.

21. The sterilization wrap as set forth in claim 13, wherein a basis weight of from 16.96 gsm to 118.69 gsm; and
said second sheet contains an absorbent material configured to allow sterilization gas to pass therethrough,
wherein said second sheet has a basis weight higher that the first sheet and greater than 118.69 gsm.

22. The sterilization wrap of claim 21, wherein the second sheet includes a high loft material.

23. The sterilization wrap of claim 21, wherein the second sheet has a higher porosity than the first sheet.

24. The sterilization wrap of claim 21, wherein the first sheet is made from a pair of laminates.

* * * * *

UNITED STATES PATENT AND TRADEMARK OFFICE
CERTIFICATE OF CORRECTION

PATENT NO. : 7,922,983 B2
APPLICATION NO. : 11/192442
DATED : April 12, 2011
INVENTOR(S) : Holly Prokash, Maya Aroch and Clarita Lewis It is certified that error appears in the above-identified patent and that said Letters Patent is hereby corrected as shown below:

Col. 12, Claim 21, line 10 reads "...a basis weight of from 16.96 gsm to 118.69 gsm; and" should read --said first sheet includes a laminate that has a basis weight of from 16.96 gsm to 118.69 gsm; and--

Signed and Sealed this
Twenty-third Day of August, 2011

David J. Kappos
*Director of the United States Patent and Trademark Office*